US008067597B2

(12) United States Patent
Wang et al.

(10) Patent No.: US 8,067,597 B2
(45) Date of Patent: Nov. 29, 2011

(54) SYNTHETIC ROUTE TO 14-HYDROXYL OPIATES THROUGH 1-HALO-THEBAINE OR ANALOGS

(75) Inventors: Peter X. Wang, Creve Coeur, MO (US); Frank W. Moser, Arnold, MO (US); Gary L. Cantrell, Troy, IL (US); Daniel P. Magparangalan, Maryland Heights, MO (US); Jian Bao, Cary, NC (US)

(73) Assignee: Mallinckrodt LLC, Hazelwood, MO (US)

( * ) Notice: Subject to any disclaimer, the term of this patent is extended or adjusted under 35 U.S.C. 154(b) by 1016 days.

(21) Appl. No.: 11/917,180

(22) PCT Filed: May 22, 2006

(86) PCT No.: PCT/US2006/019867
§ 371 (c)(1),
(2), (4) Date: Dec. 11, 2007

(87) PCT Pub. No.: WO2006/138020
PCT Pub. Date: Dec. 28, 2006

(65) Prior Publication Data
US 2008/0207906 A1    Aug. 28, 2008

Related U.S. Application Data

(60) Provisional application No. 60/691,184, filed on Jun. 16, 2005.

(51) Int. Cl.
*C07D 489/08* (2006.01)
*C07D 489/02* (2006.01)
(52) U.S. Cl. .......................................... 546/45; 546/44
(58) Field of Classification Search ................ 546/45, 546/44
See application file for complete search history.

(56) References Cited

U.S. PATENT DOCUMENTS

| | | | |
|---|---|---|---|
| 2,797,223 | A | 6/1957 | Conroy |
| 3,112,323 | A | 11/1963 | Krausz |
| 3,299,072 | A | 1/1967 | Bartels-Keith |
| 3,884,898 | A | 5/1975 | Schneider |
| 4,025,520 | A | 5/1977 | Grew et al. |
| 4,052,402 | A | 10/1977 | Calvo |
| 4,054,566 | A | 10/1977 | Rapoport et al. |
| 4,110,329 | A | 8/1978 | Rapoport et al. |
| 4,140,687 | A | 2/1979 | Grew et al. |
| 4,141,895 | A | 2/1979 | Middleton |
| 4,161,597 | A | 7/1979 | Olofson et al. |
| 4,236,008 | A | 11/1980 | Henderson |
| 4,241,065 | A | 12/1980 | Boswell, Jr. et al. |
| 4,241,066 | A | 12/1980 | Kobylecki et al. |
| 4,241,067 | A | 12/1980 | Kobylecki et al. |
| 4,272,541 | A | 6/1981 | Kotick et al. |
| 4,277,604 | A | 7/1981 | Dauben et al. |
| 4,368,326 | A | 1/1983 | Rice |
| 4,410,700 | A | 10/1983 | Rice |
| 4,521,601 | A | 6/1985 | Rice |
| 4,613,668 | A | 9/1986 | Rice |
| 4,639,520 | A | 1/1987 | Kavka |
| 4,667,037 | A | 5/1987 | Bryant, III |
| 4,795,813 | A | 1/1989 | Schwartz |
| 5,112,975 | A | 5/1992 | Wallace |
| 5,208,338 | A | 5/1993 | de Costa et al. |
| 5,300,499 | A | 4/1994 | Chow |
| 5,336,483 | A | 8/1994 | de Costa et al. |
| 5,668,285 | A | 9/1997 | Rice et al. |
| 5,756,745 | A | 5/1998 | Kavka |
| 5,869,669 | A | 2/1999 | Huang et al. |
| 5,952,495 | A | 9/1999 | Huang et al. |
| 6,008,355 | A | 12/1999 | Huang et al. |
| 6,090,943 | A | 7/2000 | Mudryk et al. |
| 6,121,296 | A | 9/2000 | Schramm et al. |
| 6,465,742 | B1 | 10/2002 | Hiraoka et al. |
| 6,723,894 | B2 | 4/2004 | Fist et al. |
| 2002/0045755 | A1 | 4/2002 | Coop et al. |
| 2006/0074239 | A1 | 4/2006 | Wang et al. |

FOREIGN PATENT DOCUMENTS

| | | |
|---|---|---|
| GB | 2392670 | 3/2004 |
| WO | WO 01/29047 | 4/2001 |
| WO | WO 03/018588 | 3/2003 |
| WO | WO 2004/108090 | 12/2004 |

OTHER PUBLICATIONS

Hosztafi et al.,Synthesis of New Apomorphine Derivatives Containing Halogen (CI and Br) in Ring-d#, Synthetic Communications, 26(21), 1996, pp. 3909.
Database Crossfire Beilstein Beilstein Institut Zur Foederung Der Chemischen Wissenschaften, Frankfurt Am Main, DE; Database-Accession No. 5638882 (reaction ID) XP002399882, abstract & Chemische Berichte, vol. 56, 1924, p. 1406 (From Search Report).
White et al., "Biomimetic Total Synthesis of (−)-Codeine", Tetrahedron, 1983, vol. 39, No. 14, pp. 2393-2397 XP001180217 (From Search Report).
Krassnig et al., "Optimization of the Synthesis of Oxycodone and 5-Methyloxycodone", Archiv Der Pharmazie, Verlag Chemie. Weinheim, DE, 1996, vol. 329, pp. 325-326 XP008055004 (From Search Report).

*Primary Examiner* — Charanjit Aulakh

(57) ABSTRACT

Novel methods of synthesis of known and novel 14-hydroxyl opiates through 1-halothebaine and derivatives are described.

8 Claims, No Drawings

SYNTHETIC ROUTE TO 14-HYDROXYL OPIATES THROUGH 1-HALO-THEBAINE OR ANALOGS

CROSS REFERENCE TO RELATED APPLICATIONS

This application is a national stage application of PCT/US2006/019867, filed May 22, 2006, which claims the benefit of U.S. Provisional Application No. 60/691,184 filed Jun. 16, 2005.

BACKGROUND OF THE INVENTION

The present invention relates to a method for the production of 14 hydroxyl-opiates, and more particularly to a method of producing 14-hydroxyl-opiates through 1-halo-northebaine derivatives.

An example of a 14-hydroxyl-opiate is oxycodone. Oxycodone is a semi-synthetic opioid agonist that is used as an alternative to morphine in controlling severe acute postoperative or posttraumatic pain or cancer pain. Oxycodone is currently commercially produced in two steps from thebaine which is extracted from a natural source or synthetically derived from a natural product. The synthetic thebaine is made in at least three steps from hydrocodone that is generated in two steps from codeine.

In more general terms, conventional methods for producing 14-hydroxyl-opiates typically involve multi-step synthetic methods that are expensive and inefficient. Attempts to improve efficiency have included the use of transition metal oxidants such as ruthenium tetraoxide, manganese(IV)oxide, and catalytic cobalt compounds with oxygen or air on codeine or derivatives of morphine followed by reduction of the resultant 14-hydroxyl-codeinone. Overall, these oxidative methods result in low yield due in part to difficult isolations from complex mixtures of byproducts in remaining inorganic salts, and suffer from poor reproducibility.

Enzymatic methods of conversion have also been attempted, but these methods, because of the low concentrations of opiate substrate in the reaction medium and slow kinetics, are costly and difficult to scale up.

The conventional route to preparing thebaine is disclosed in the literature as follows:

Scheme 1
Coventional Route for making thebaine

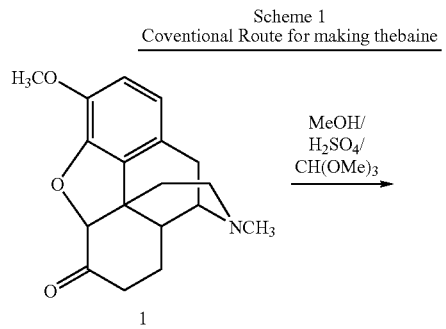

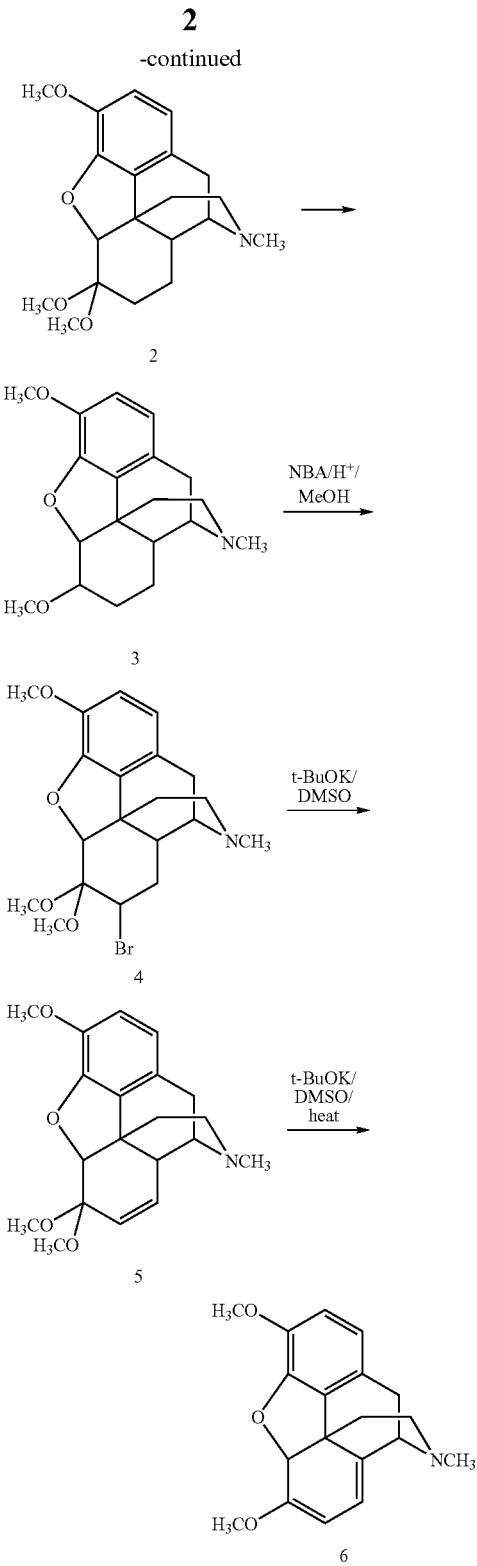

Similarly, 1-bromothebaine has reportedly been synthesized from Formula 7 as follows:

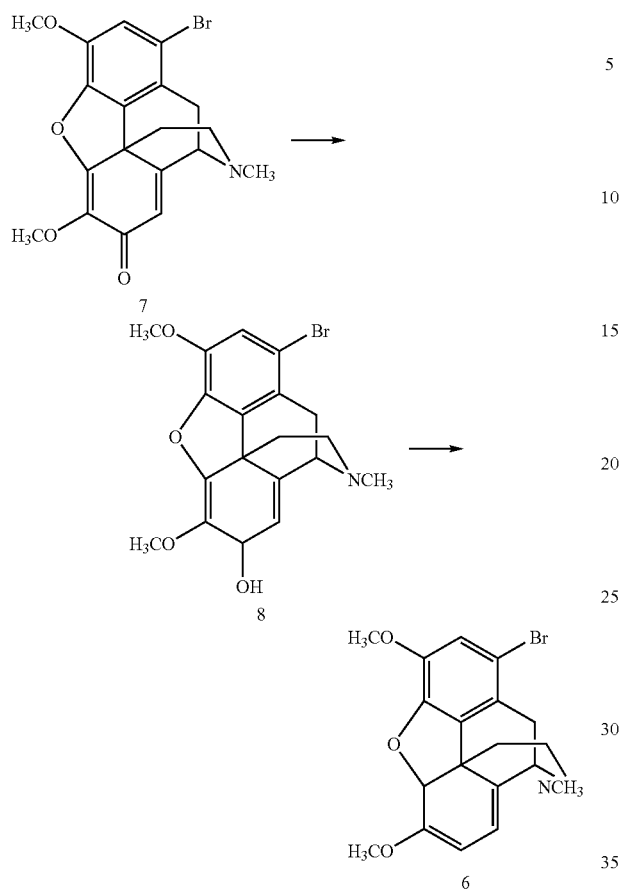

There is therefore a need for an improved method of conversion that is easily scaled up and economical for manufacturing purposes.

SUMMARY OF THE INVENTION

One aspect of the present invention is to provide a totally synthetic option to the use of naturally derived thebaine and more efficient pathways for the preparation of 14-hydroylated opiate products including but not limited to oxycodone, oxymorphone, naloxone, nalmefene, nalbuphine, naltrexone and the useful product intermediate noroxymorphone.

An aspect of the present invention utilizes a transition metal complex of the formula $[M(PR^4R^5R^6)_nX_m]_p$; wherein M is a Group VIII transition metal; $R^4$, $R^5$ and $R^6$ are selected from the group consisting of alkyl, aryl, alkoxyl, phenoxyl and combinations thereof; X is a halide or an anion; n is 1, 2, 3 or 4; m is 1 or 2; and p is at least 1.

These are merely illustrative aspects of the present invention and should not be deemed an all-inclusive listing of the innumerable aspects associated with the present invention. These and other aspects will become apparent to those skilled in the art in light of the following disclosure.

DETAILED DESCRIPTION

In an illustrative embodiment of the present invention there is provided a method for the conversion of 14-hydroxyl-opiates through 1-halo-thebaine derivatives, as shown in Scheme 3, below.

-continued

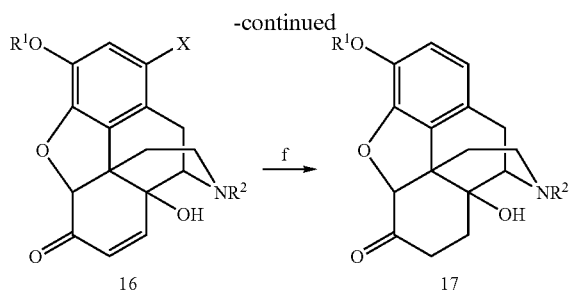

Step a is the preparation of a composition according to Formula 10 in a "one-pot" synthesis from a composition according to Formula 9,

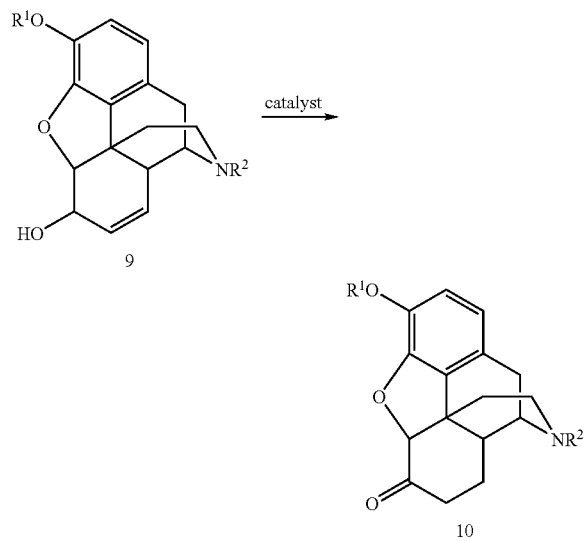

wherein $R^1$ is a member of but not limited to H, a benzyl, a substituted benzyl, an alkyl, an aryl, an acyl, an alkoxycarbonyl, an aminocarbonyl, trialkylsilyl, tetrahydropyranyl or tetrahydrofuranyl group;

$R^2$ is H, a benzyl group, an aryl group, an acyl group, a formyl group, an alkoxycarbonyl or an aminocarbonyl group; and $R^3$ is an alkyl group, including but not limited to C1-C6 alkyl group derived from an alcohol including but not limited to methanol, ethanol, n-propanol, and n-butanol, or two $R^3$ groups taken together can form a cyclic bridging group derived from diols including but not limited to ethylene glycol and propylene glycol; an aryl group or an acyl group.

In this embodiment of the present invention a composition of Formula 9 is catalytically converted to a composition of Formula 10 in the presence of at least one transition metal complex of the formula $[M(PR^4R^5R^6)_nX_m]_p$; wherein M is a Group VIII transition metal; $R^4$, $R^5$ and $R^6$ are selected from the group consisting of alkyl, aryl, alkoxyl, phenoxyl and combinations thereof; X is a halide or an anion; n is 1, 2, 3 or 4; m is 1 or 2; and p is at least 1. The catalysts of the present invention are the subject matter of pending U.S. patent application Ser. No. 10/495,503, filed Nov. 5, 2003, and incorporated herein in its entirety.

Step b) of the overall Scheme 3 is the only known example of the conversion of a composition according to Formula 9 into a composition according to Formula 13 in a "single pot"

reaction. Step b) comprises the execution of step a) followed by halogenating the resulting composition according to Formula 10 with at least one halogenating reagent in at least one protic solvent in the presence of $R^7C(OMe)_3$ and at least one acid to form a composition according to Formula 13;

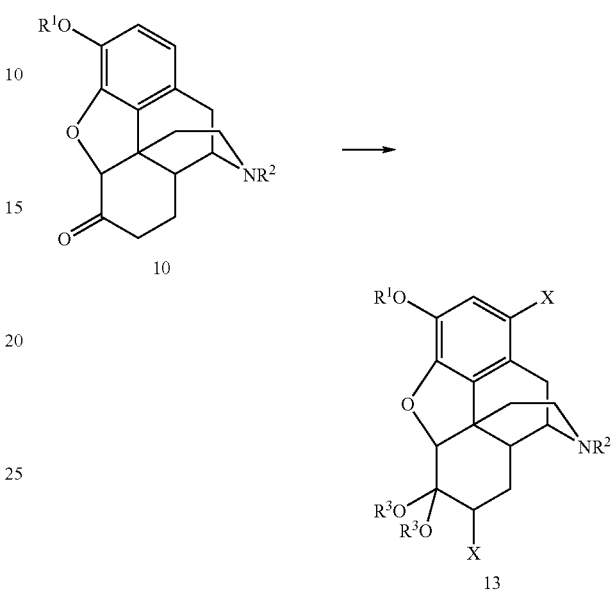

R may be selected from H, alkyl or alkoxy and the acid is any mild or strong acid capable of resulting in the desired conversion. Suitable acids or Lewis acids include but are not limited to sulfuric acid ($H_2SO_4$) phosphoric acid ($H_3PO_4$), methanesulfonic acid ($MeSO_3H$), p-toluenesulfonic acid, trifluoroacetic acid, trifluoromethanesulfonic acid, hydrogen chloride (HCl), hydrogen bromide (HBr), tetrafluoroboric acid ($HBF_4$) and mixtures thereof or Lewis acids, $BF_3$, $PCl_5$ or $POCl_3$. Any suitable halogenation reagent as are known in the art may be used. Suitable halogenation reagents include but are not limited to chlorine ($Cl_2$), bromine ($Br_2$), N-bromoacetamide (NBA), N-bromosuccinimide (NBS), 1,3-dibromo-5,5-methylhydantoin (DBDMH,) 1,3-dichloro-5,5-methylhydantoin (DCDMH,), N-chlorosucccimide (NCS), pyridinium tribromide. The halogenations are carried out in a suitable solvent or mixture of solvents. Suitable solvents include but are not limited to chloroform, dichloromethane, acetonitrile, methanol, chlorobenzene and mixtures thereof.

Step c) comprises reacting the composition according to Formula 13 with less than about two equivalents of at least one base to form a composition according to Formula 14;

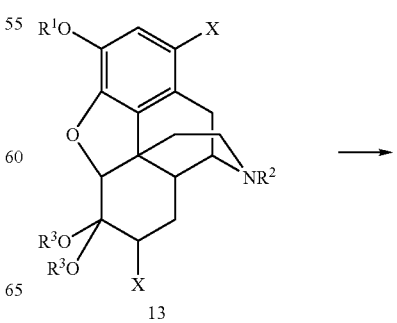

-continued

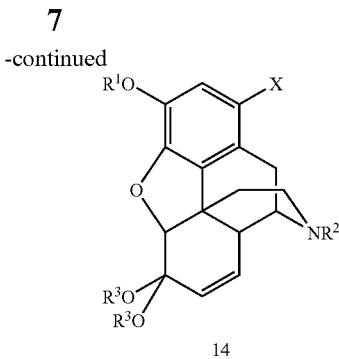
14

Suitable bases include but are not limited to salts of alkoxides, hydroxides, amides, anhydrous fluoride and carbonate. In some preferred embodiments, a phase transfer agent may be used to facilitate the transport of the inorganic base into the reaction media and to magnify the basicity of the anion. Such a phase transfer agent includes but is not limited to 18-crown-6, tetraalkylammonium salts, pyridinium salts, imidazolium salts, N,N-dialkylaminopyridinium salts, and substituted analogs.

Step d) involves heating the composition according to formula 14 in the presence of at least one acid to from a composition according to Formula 15;

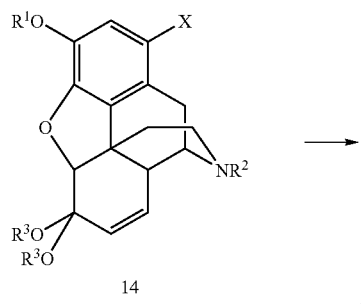
14

→

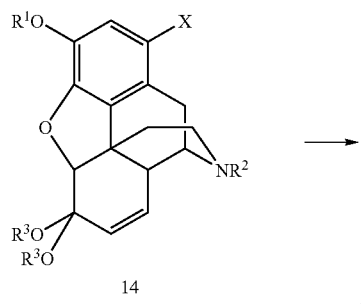
15

The conversion of Formula 14 into formula 15 occurs in the presence of an acid or a Lewis acid selected from the group including but is not limited to glacial acetic acid(HOAc), formic acid($HCO_2H$), n-propanoic acid, $RCO_2H$, wherein R is alkyl, or aryl, methanesulfonic ($MeSO_3H$), p-toluene-sulfonic acid, trifluoroacetic acid ($CF_3CO_2H$), phosphoric acid, sulfuric acid, $PCl_5$ and $POCl_3$. Combinations of an acid with a protic solvent should be avoided at this step so that hydrolysis to the codeinone-type by-product is minimized or prevented. It is noted that in the presence of a base in addition to prolonged heating, significant losses of Formula 15 have been observed.

As illustrative of another aspect of the enablement of these inventions, a composition of Formula 15 is prepared in "one-pot" from a composition of Formula 13. Herein, "one-pot" is meant to refer to more than one chemical transformation performed within a single manufacturing vessel before isolation of an intermediate or product.

Step e) of reaction Scheme 1 comprises oxidizing a composition according to Formula 15 with at least one oxidizing agent to form a composition according to Formula 16;

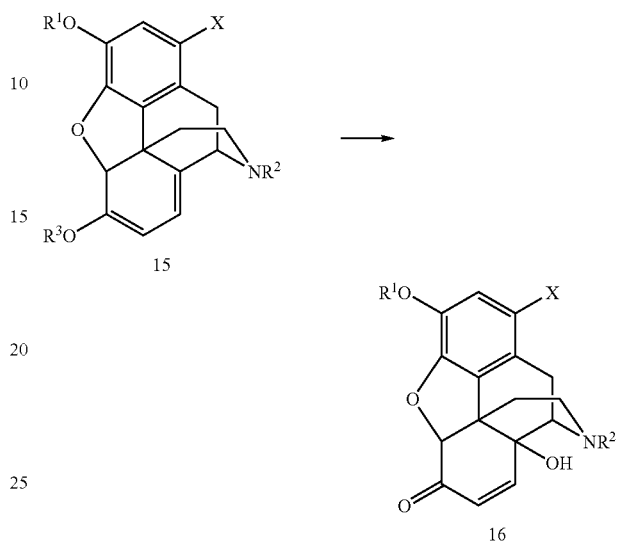

Suitable oxidizing agents include but are not limited to hydrogen peroxide solution, peroxyacetic acid, 3-chloroperoxybenzoic acid, $RCO_3H$(R is H, an alkyl, or an aryl) or optionally the in situ peroxyacid preparation using a carboxylic acid and hydrogen peroxide.

Step f) of Scheme 3 discloses reducing the composition according to Formula 16 with at least one reductive agent to form the composition according to Formula 17;

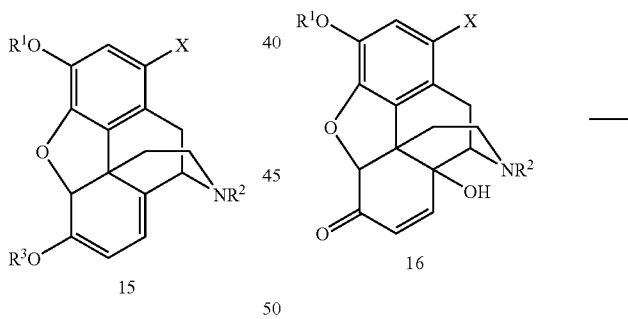

Suitable reductive reagents includes but not are not limited to a combination of pressurized hydrogen or formic and a metal supported catalyst such as M/C, wherein M is Pd, Pt, Ru, or Rh and C is carbon, as well as other conventional reductive reagents as are well known in the art.

These inventions, as illustrated in Scheme 3 and described above provide a totally synthetic option to the use of naturally derived thebaine and more efficient pathways for the preparation of a host of 14-hydroxylated opiate products; for example, oxycodone oxymorphone, naloxone and naltrexone.

In another embodiment of the present invention, there is provided a "one-pot" method for the conversion of a composition according to Formula 9 into a composition according to Formula 13, as described in detail above.

In a further embodiment of the present invention, there is provided a "one-pot" method for the conversion of a composition according to Formula 13 into a composition according to Formula 15.

In yet another embodiment of the present invention, there is provided a "one-pot" method for the conversion of a composition according to Formula 13 into a composition according to Formula 16.

In yet another embodiment of the present invention, there is provided a "one-pot" method for the conversion of a composition according to Formula 14 into a composition according to Formula 17.

In another embodiment of the present invention, a composition according to Formula 15 is oxidized to form N-oxides according to Formula 16-N—Os;

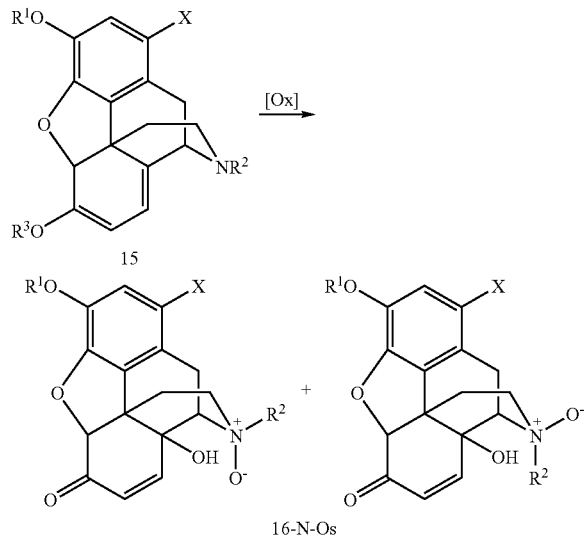

In another embodiment, a composition according Formula 16 or a composition according to Formula 16-N—Os is converted into a composition according to Formula 17, by reducing the composition according to Formula 16 or Formula 16-N—Os or salts thereof with at least one reductive agent to form the composition according to Formula 17;

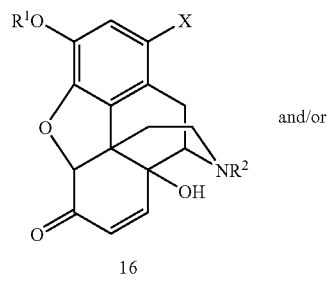

and/or

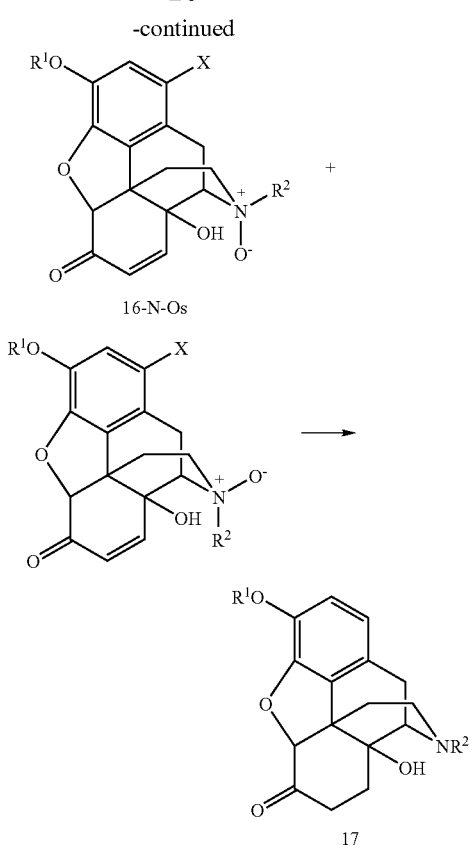

wherein $R^1$ is H, a benzyl group, an aryl group, an acyl group, an alkoxycarbonyl group or tetrahydropyranyl group and $R^2$ is H, a benzyl group, an aryl group, and an acyl group.

It is note depending on the conditions, when $R^1$ is a benzyl group, reduction can lead to elimination of benzyl to H. If the N-oxides are treated with certain metal ions like Fe(II/III) when $R^2$ is a methyl, a Modified NonClassical Polonovski Reaction occurs giving the NH group norhalothebaine analog (for N-demethylations), as referred to in JOC Vol. 68, No. 25 (2003) 9847. Under neutral pH, the oxidation of the 1-halothebaines analogs will give the corresponding N-oxides in high yield. Over oxidation with peracid provides the 14-hydroxycodeinone N-oxide derivatives where $R^2$ may come from the recited list. Alternatively, the 14-hydroxycodeinone may be oxidized separately using hydrogen peroxide to it corresponding N-oxides, in this instance, 1-halo-14-hydroxycodeinone derivatives with R's from the recited lists.

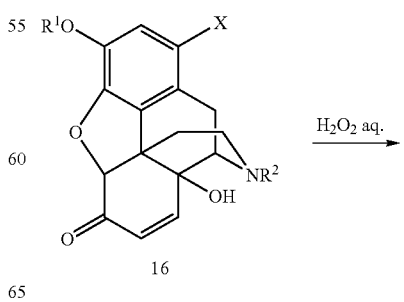

-continued

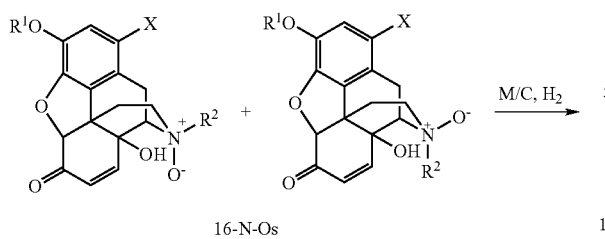

16-N-Os

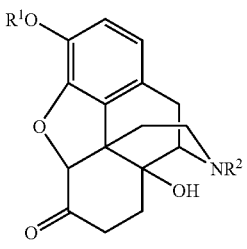

17

It has been reported in the art that nor-N-oxides when treated with Fe(II) in formic acid affords the oxazolidine compound. The oxazolidine may be hydrolyzed back to the nor-compound so could act a nitrogen protecting group. Some of the compositions of the present invention would react similarly where $R^2$ is a hydrogen (H). A non-limiting illustrative reaction is as follows:

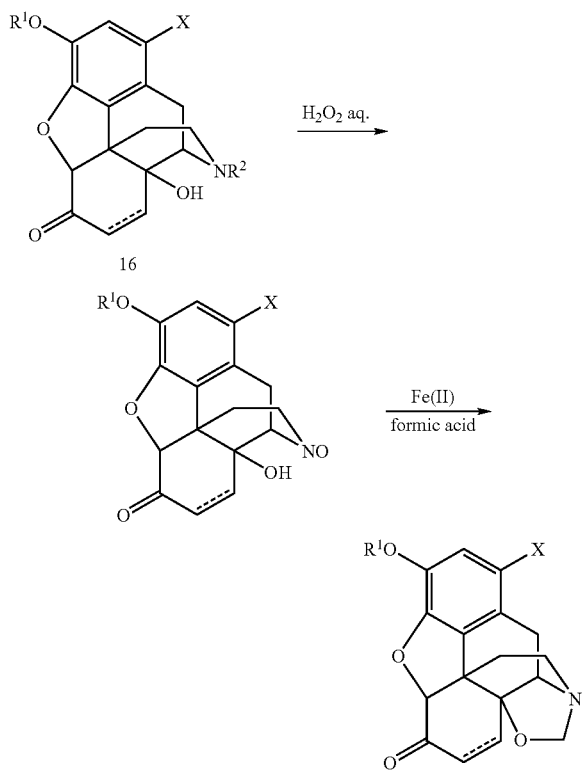

The novel intermediates of Formulas 10 through 16 are given in the general Formula 29, below:

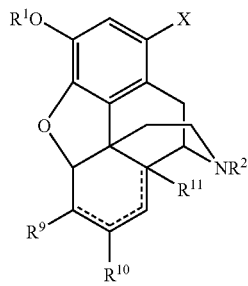

wherein $R^1$ is H, $CH_3$, $PhCH_2$, $R^8Co$, $R^8OCO$ or THP;
$R^2$ is H, $CH_3$, $PhCH_2$, CHO, $R^8CO$, $R^8OCO$;
$R^3$ is C1-4 alkyl, aryl or acetate;
$R^8$ is C1-6 alkyl;
$R^9$ is

as part of a ketal;

as a part of an enol ether or acetate; or

as part of a ketone;
$R^{10}$ is H, Cl or Br; and
$R^{11}$ is H or OH.

An illustrative embodiment of the inventions herein described is the preparation of oxycodone from 1-bromothebaine. The 1-bromothebaine is made in a "one pot" reaction from 1,7-dibromo-hydrocodone dimethyl ketal, that in turn is generated in "one pot" by sequential reactions from codeine. The details of this illustrative synthesis are given in the examples, below. It is noted that the preparation of 1-bromothebaine in a "one-pot" reaction from codeine avoids the inherent difficulties of preparing and isolating the very moisture sensitive enol ether intermediate of Formula 3, wherein $R^1$ and $R^2$ are methyl groups, as illustrated in the conventional reaction Scheme 1.

Similarly, oxymophone, noroxymorphone and derivatives can be synthesized as shown in Scheme 3. Oxymorphone is prepared from morphine as shown in scheme 3. The phenol group of morphine is protected using a benzyl ($PhCH_2$) group or acyl (RCO) group. In the case of $PhCH_2$ as protecting group, oxymorphone is made directly after hydrogenation of Formula 16 ($R^1=PhCH_2$). Alternatively, the O-acylated oxymorphone (Formula 17, $R^1=RCO$ and $R^2=Me$) provides O-acylated oxymorphone that is easily hydrolyzed to oxymorphone. If noroxymorphone is the target product, then the $PhCH_2$ protected morphine derivative (Formula 9, $R^1=R^2=PhCH_2$ or $R^1=RCO$ and $R^2=PhCH_2$) is used as the starting material.

Many process designs, as are well known in the art, could be utilized with the process of the present invention.

EXAMPLES

Example 1

To a 1000 mL three-necked flask, MeOH (250 mL) was added. Codeine (62.5 g, 0.209 mol) was added and stirred until completely dissolved. The solution was flushed with nitrogen over a 10 minute period. Wilkenson's catalyst, Rh(PPh$_3$)$_3$Cl, (0.625 g) was added under nitrogen. The solution was refluxed for 3 h to give a suspension. MeOH (125 mL) was removed by distillation. The suspension was cooled to 50° C. CH(OMe)$_3$ (125 mL) and H$_2$SO$_4$ (14.2 mL) were added. The temperature was maintained under 62° C. during the addition of H$_2$SO$_4$. After refluxing for 30 min., the solution was cooled to 50° C. A solution of Br$_2$ (23.63 mL, 0.46 mol) in CHCl$_3$ (125 mL) was added over 45 min. and the temperature was maintained at or around 50° C. for 30 min after this addition was complete. The solution was filtered. The filtrate and CHCl$_3$ (125 mL) was added to a stirred solution of 29% NH$_4$OH (188 mL) and water (188 mL) held at 0-5° C. for about 10 min until two layers formed. The aqueous layer was extracted with CHCl$_3$ (125 mL). The organic layers were washed with water (3×313 mL) and taken to dryness under reduced pressure to give 115 g of a sticky solid. The solid was dissolved in MeOH (188 mL) and taken to dryness under reduced pressured to provide 104 g of the crude product 13 as a foam (yield of crude product>99%, purity>92% area/area by HPLC).

Example 2

The 1,7-dibromohydrocodone dimethyl ketal (13, 80.0 g, 0.159 mmol) was dissolved in 1-methyl-2-pyrrolidinone (NMP, 120 mL), flushed with nitrogen for 10 min and cooled to 5~10° C. KOBu-t (26.8 g, 0.24 mol) was added in three portions. Since the reaction was exothermic, the temperature was maintained under 45° C. by controlling the addition rate. The mixture was stirred at 40~45° C. for 1 h after the addition and then cooled to rt. Glacial acetic acid (HOAc, 180 mL) was then added. The solution was heated to 100° C. for 6 h. HOAc (~100 mL) was removed by distillation. The solution was poured into a iced water (480 mL), followed by a toluene (120 mL) wash. Toluene (480 mL) was added to the aqueous layer. NaOH (50%) was added until the pH=12.3. The organic layer was washed with water (5×480 mL). The product in the organic layer was assayed to contain 41.5 g (purity 88% area/area by HPLC). The crude product of 21 was isolated as a brown solid (45 g).

Example 3

Compound 15 (5.00 g, 12.8 mmol) was dissolved in HOAc (15 mL). Peroxyacetic acid (CH$_3$CO$_3$H~20%, freshly made from HOAc/H$_2$O, 7.2 mL, ~19 mmol) was added dropwise at 25-30° C. Stirring at rt was continued for another 50 min after the complete addition. 5% Pd/C (0.25 g) was added and stirred at rt for 2 h followed by another addition of 5% Pd/C (0.75 g). The reactor was flushed with nitrogen three times and then hydrogen three times. The reactor was heated to 60° C. under hydrogen 60 psi for 12 h. The suspension was filtered. The solid was washed with MeOH (2×5 mL). The combined filtrates were taken almost dryness under reduced pressure. Ethyl acetate (20 mL)/5% NH$_4$OH (20 mL, final pH>10) was added. The aqueous layer was extracted with ethyl acetate (20 mL). The combined organic layers were washed with water (3×10 mL), and taken to dryness under reduced pressure to give 3.3 g of solid crude product 17.

Compound 17 was re-crystallized from ethyl acetate/heptane to give 1.72 g of pure product as a white crystalline solid.

From the foregoing description those skilled in the art will appreciate that economical and efficient methods for the synthesis of known and novel 14-hydroxyl opiates are provided.

The invention claimed is:
1. A one-pot process for the conversion of a compound according to Formula 14 into a compound according to Formula 17, the process comprising:
   a) heating the compound according to formula 14 in the presence of at least one acid to form a compound according to formula 15;

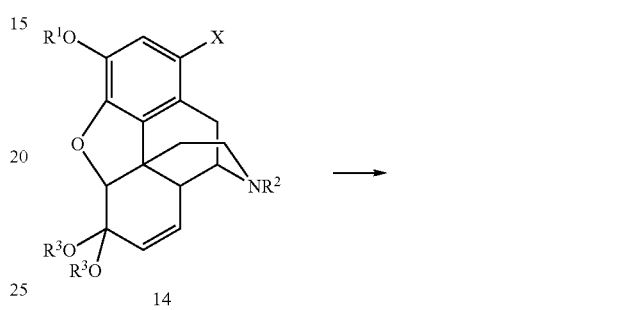

14

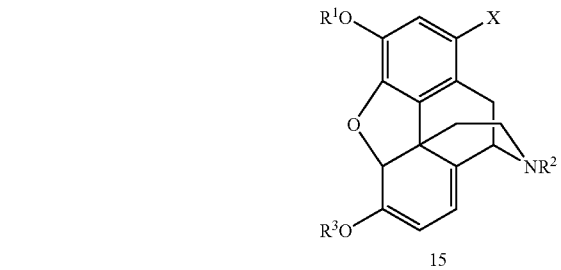

15 b) oxidizing the compound according to Formula 15 with at least one oxidizing agent to form a compound according to Formula 16; and

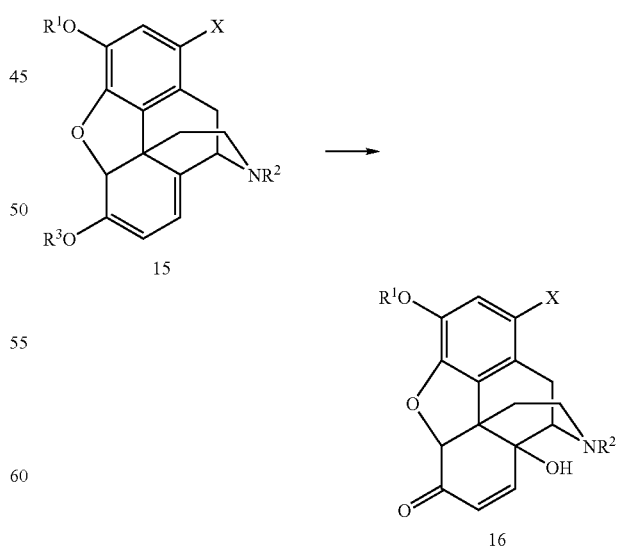

15

16 c) reducing the compound according to Formula 16 with at least one reductive agent to form a compound according to Formula 17;

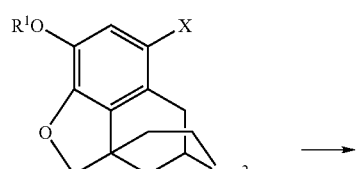

16

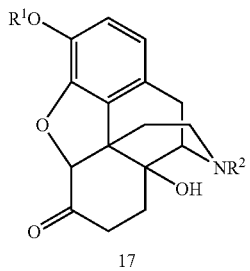

17 wherein $R^1$ is H, methyl, a benzyl group, an aryl group, an acyl group, an alkoxycarbonyl group or tetrahydropyranyl group;

$R^2$ is H, methyl, a benzyl group, an aryl group, an acyl group, a formyl group, a formyl ester, an alkoxycarbonyl group or alkylamidocarbonyl group;

$R^3$ is H, an alkyl group, an aryl group or an acyl group; and,

X is a halogen.

2. The process of claim 1, wherein the process is for the preparation of compounds according to Formula 17, the process additionally comprising:

a) catalytically converting a compound according to Formula 9 into a compound according to Formula 10 in the presence of at least one catalyst, wherein the catalyst is at least one transition metal complex of the formula $[M(PR^4R^5R^6)_nX_m]_p$; wherein M is a Group VIII transition metal; $R^4$, $R^5$ and $R^6$ are selected from the group consisting of alkyl, aryl, alkoxyl, phenoxyl and combinations thereof; X is a halide or an anion; n is 1, 2, 3 or 4; m is 1 or 2; and p is at least 1;

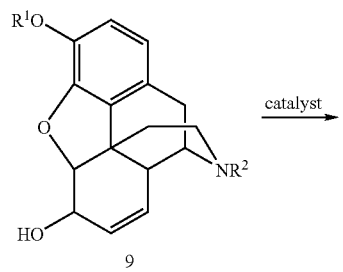

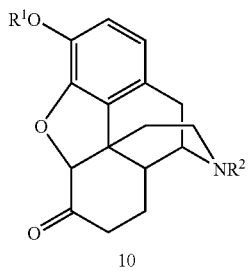

b) halogenating the compound according to Formula 10 with at least one halogenating reagent in at least one protic solvent in the presence of $R^7C(OR^3)_3$, wherein $R^7$ is H, an alkyl or an alkoxy, and at least one first acid to form a compound according to Formula 13;

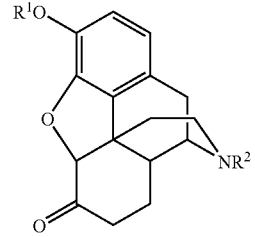

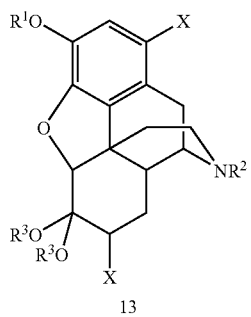

c) reacting the compound according to Formula 13 with less than about two equivalents of at least one base to form a compound according to Formula 14; and

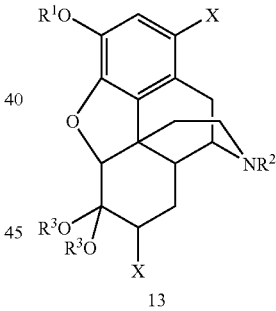

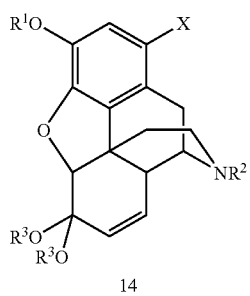

d) heating the compound according to formula 14 in the presence of at least one second acid to from a compound according to Formula 15.

3. The process of claim 2 wherein the at least one first acid includes an acid selected from the group consisting of sulfuric acid ($H_2SO_4$), phosphoric acid ($H_3PO_4$), methanesulfonic acid ($MeSO_3H$), p-toluenesulfonic acid, trifluoroacetic acid, trifluoromethanesulfonic acid, hydrogen chloride (HCl), hydrogen bromide (HBr) and mixtures thereof;

the at least one halogenating reagent includes a halogenating reagent selected from the group consisting of bromine ($Br_2$), N-bromoacetamide (NBA), N-bromosuccinimide (NBS), 1,3-dibromo-5,5-dimethylhydantoin (DBDMH), 1,3-dichloro-5,5-dimethylhydantoin (DCDMH), N-chlorosuccinimide (NCS) and mixtures thereof;

the at least one second acid includes an acid selected from the group consisting of HOAc, $HCO_2H$, $RCO_2H$ wherein R is an alkyl, benzyl or aryl, $MeSO_3H$, p-toluenesulfonic acid, $CF_3CO_2$, $POCl_3$ and mixtures thereof;

the at least one oxidizing agent includes an oxidizing agent selected from the group consisting of hydrogen peroxide solution, peroxyacetic acid, 3-chloroperoxybenzoic acid, $RCO_3H$ wherein R is H, an alkyl, or an aryl, and mixtures thereof; and the at least one reductive agent includes a reductive agent selected from the group consisting of a combination of pressurized hydrogen on metal supported catalyst having the formula M/C, wherein M is Pd, Pt, Ru, or Rh and C is carbon.

4. The process of claim 1, wherein:

$R^1$ is H, $CH_3$, $PhCH_2$, $R^8CO$, $R^8OCO$ or a tetrahydropyranyl group;

$R^2$ is H, $CH_3$, $PhCH_2$, CHO, $R^8CO$ or $R^8OCO$;

$R^8$ is $C_{1-6}$ alkyl;

$R^3$ is $C_{1-4}$ alkyl or acetate; and

X is Cl or Br.

5. The process of claim 1 wherein the at least one oxidizing agent includes an oxidizing agent that is selected from the group consisting of hydrogen peroxide solution, peroxyacetic acid, 3-chloroperoxybenzoic acid, $RCO_3H$ wherein R is H, and alkyl, or an aryl, and mixtures thereof.

6. The process of claim 1, wherein in step (b), $R^3$ in $R^7C(OR^3)_3$ is Me.

7. The process of claim 6, wherein $R^1$ and $R^2$ are methyl and X is Br.

8. The process of claim 2, wherein the at least one reductive agent includes a reductive agent selected from the group consisting of a combination of pressurized hydrogen on metal supported catalyst having the formula M/C, wherein M is Pd, Pt, Ru, or Rh and C is carbon.

* * * * *